(12) United States Patent
Molden et al.

(10) Patent No.: US 10,046,130 B2
(45) Date of Patent: Aug. 14, 2018

(54) AIRWAY-TUBE HOLDER

(71) Applicant: Laerdal Medical AS, Stavanger (NO)

(72) Inventors: Mathias Molden, Stavanger (NO); Robert Provo Kluit, Stavanger (NO)

(73) Assignee: LAERDAL MEDICAL AS, Stavanger (NO)

( * ) Notice: Subject to any disclaimer, the term of this patent is extended or adjusted under 35 U.S.C. 154(b) by 513 days.

(21) Appl. No.: 14/718,768

(22) Filed: May 21, 2015

(65) Prior Publication Data

US 2016/0339194 A1 Nov. 24, 2016

(51) Int. Cl.
| | |
|---|---|
| *A61M 16/04* | (2006.01) |
| *F16B 2/06* | (2006.01) |
| *A61M 25/02* | (2006.01) |
| *F16B 37/08* | (2006.01) |

(52) U.S. Cl.
CPC .... *A61M 16/0497* (2013.01); *A61M 16/0493* (2014.02); *F16B 2/065* (2013.01); *A61M 2025/022* (2013.01); *F16B 37/0857* (2013.01)

(58) Field of Classification Search
CPC .......... A61M 16/0497; A61M 16/0493; A61M 2025/022; F16B 2/065; F16B 37/0857
USPC .................................................... 128/202.27
See application file for complete search history.

(56) References Cited

U.S. PATENT DOCUMENTS

| | | | |
|---|---|---|---|
| 2,671,482 | A | 3/1954 | Gordon |
| 3,602,227 | A | 8/1971 | Andrew |
| 4,934,889 | A | 1/1990 | Kurosaki |
| D323,390 | S | 1/1992 | Paine et al. |
| 5,402,776 | A | 4/1995 | Islava |
| 5,513,633 | A | 5/1996 | Islava |
| D373,823 | S | 9/1996 | Baldwin |
| D395,505 | S | 6/1998 | Noonan et al. |
| 5,928,198 | A | 7/1999 | Lester |
| 5,954,707 | A | 9/1999 | Kanesaka et al. |
| 5,957,883 | A | 9/1999 | Lin |

(Continued)

FOREIGN PATENT DOCUMENTS

| | | |
|---|---|---|
| EP | 1400709 A1 | 3/2004 |
| WO | 2014062012 A1 | 4/2014 |

OTHER PUBLICATIONS

Authorized Officer: Corine Le Bolloch, "International Search Report and Written Opinion" dated Aug. 17, 2016 issued in counterpart PCT Application No. PCT/IB2016/052983, Publisher: PCT, Published in: EP.

(Continued)

*Primary Examiner* — Andrew S Lo
(74) *Attorney, Agent, or Firm* — Kaplan Breyer Schwarz, LLP

(57) ABSTRACT

An air-way tube holder includes a face plate having a v-shaped tube-receiving surface that aligns with one side of an opening through the face plate, and a holding block, which is disposed near a second side of the opening. The holding block receives a thumb screw and an engagement arm, the latter including a clamping head, which directly opposes the tube-receiving surface. The thumb screw is adapted to move the clamping head toward the tube-receiving surface to immobilize an airway tube therebetween, either by sliding the thumb screw (gross adjustment) or turning the thumb screw (fine adjustment). The thumb screw/clamping head is releasable by actuating a quick-release mechanism.

28 Claims, 18 Drawing Sheets

(56) References Cited

U.S. PATENT DOCUMENTS

| | | | |
|---|---|---|---|
| 6,010,484 | A | 1/2000 | McCormick et al. |
| 6,067,985 | A | 5/2000 | Islava |
| 6,612,309 | B1 | 9/2003 | Ancona |
| 6,634,359 | B1 | 10/2003 | Rudy, Jr. et al. |
| D528,657 | S | 9/2006 | Adams et al. |
| D528,659 | S | 9/2006 | Cherfas et al. |
| 7,437,804 | B1 | 10/2008 | Geiger et al. |
| 7,517,340 | B2 | 4/2009 | Barrientos |
| 8,360,063 | B2 | 1/2013 | Liland |
| 8,636,008 | B2 | 1/2014 | Flory et al. |
| D750,773 | S | 3/2016 | Eaton et al. |
| D753,516 | S | 4/2016 | Le Gall |
| D762,300 | S | 7/2016 | Breitweiser et al. |
| 9,707,364 | B2 * | 7/2017 | Islava ............... A61M 16/0497 |
| 2009/0028668 | A1 | 1/2009 | Luk |
| 2009/0229616 | A1 * | 9/2009 | Liland ............... A61M 16/0488 |
| | | | 128/207.14 |

OTHER PUBLICATIONS

"Non Final Office Action" dated Jan. 17, 2018 in Design U.S. Appl. No. 29/556,471.

\* cited by examiner

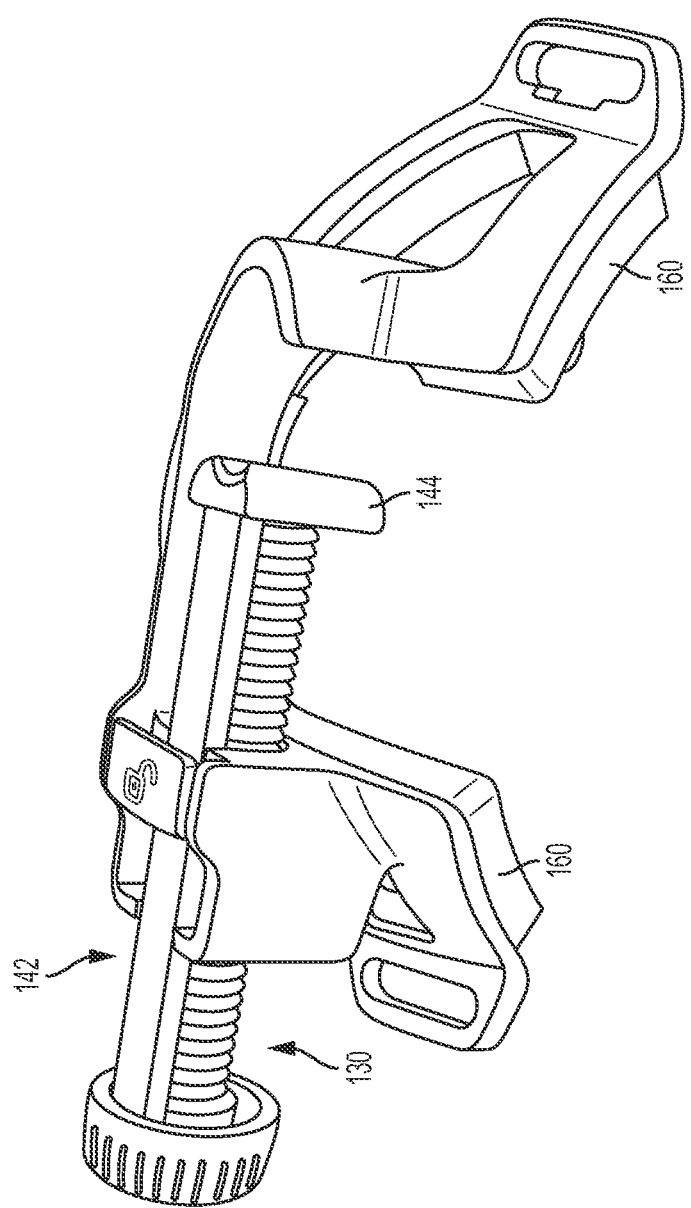

AIRWAY-TUBE HOLDER

FIELD OF THE INVENTION

The present invention relates to an apparatus for stabilizing an airway tube.

BACKGROUND OF THE INVENTION

Endotracheal tubes and laryngeal tubes establish and maintain an airway in a patient for the exchange of oxygen and carbon dioxide. These tubes are commonly used to mechanically ventilate a patient's lungs during general anesthesia and resuscitation. They are also used in critical-care and emergency-medicine settings.

Once inserted, the airway tube must be secured to prevent the tube from moving in patient's throat during treatment. A variety of devices have been proposed for this purpose. Most of the recently proposed devices include a face plate having special adaptations for receiving and immobilizing the airway tube. In some of these devices, the face plate includes a "v-" or "u-" shaped tube-receiving surface that aligns with an opening through the face plate.

In use, after inserting an airway tube into a patient, a caregiver positions the face plate over the patient's face. The portion of the airway tube exiting the patient's oral cavity is positioned near the tube-receiving surface of the face plate. The caregiver then advances a clamping head towards the airway tube until they engage. Sandwiched between the clamping head and the tube-receiving surface, the airway tube is immobilized.

The clamping head is advanced using an actuating device, which the caregiver manipulates to move the clamping head into proper position. The most common implementations of the actuating device are a thumb screw or a ratchet assembly. Some examples of airway-tube holders that incorporate a thumb screw are disclosed in U.S. Pat. Nos. 5,402,776; 5,513,633; 6,067,985; and 8,360,063. Some examples of airway tube holders that use a ratchet assembly are disclosed in U.S. Pat. Nos. 6,010,484; 6,634,359 and in PCT Publication WO 2014/062012.

These and other prior-art airway tube holders have proven to be effective at immobilizing and stabilizing an airway tube. Yet they are, to varying degrees, uniformly cumbersome to use. As a consequence, the art would benefit from improvements in the ergonomics and other aspects of the design of airway-tube holders.

SUMMARY OF THE INVENTION

The present invention provides an airway-tube holder that overcomes some of the drawbacks of the prior art.

The inventors studied conventional airway-tube holders to identify their shortcomings. The inventors came to realize that the actuating device (e.g., thumb screw, ratcheting mechanism, etc.) of most prior-art airway-tube holders impedes the ability of a caregiver to rapidly immobilize an airway tube or quickly withdraw it from a patient.

In particular, having to rotate a thumb screw multiple times until a clamping head abuts an airway tube, or until it retracts therefrom, takes time. Furthermore, in some airway-tube holders, the screw or ratcheting mechanism is loosely coupled to the face mask until it advances at least part of the way toward the airway tube. In such cases, it can be awkward to begin the process of advancing the actuating device, such that two hands are required and time is lost. In medical emergencies, such delays are often more than a simple inconvenience; rather, they can be life threatening.

An airway-tube holder in accordance with the illustrative embodiment of the present invention addresses the aforementioned problems with:
improved ergonomics;
a thumb screw that can be advanced simply by pushing;
a thumb screw that can be released via a quick-release feature, among other features.

In accordance with the illustrative embodiment, the airway tube holder comprises a face plate having a v-shaped tube-receiving surface, in the form of a notch, which aligns with one side of an opening through the face plate. The face plate includes a holding block, which is disposed near a second side of the opening. The holding block receives a thumb screw and an engagement arm. The engagement arm includes a clamping head, which directly opposes the tube-receiving surface. The thumb screw, which is operatively coupled to the engagement arm, is adapted to move the clamping head toward the tube-receiving surface. The clamping head and tube-receiving surface thus collectively form a clamp or adjustable aperture for immobilizing an airway tube.

The thumb screw is normally engaged to one or more complementary female screw threads. However, by virtue of the arrangement of the female screw thread(s) with respect to the thumb screw, and as a consequence of the thumb screw's thread profile, the thumb screw can be readily slid into position. This occurs without the need to take steps to actively disengage the female screw threads from the thumb screw. Once the clamping head of the engagement arm is in abutting or near-abutting relation with the sidewall of an airway tube, the thumbscrew can then be turned by hand (i.e., threaded) to finely adjust the amount of pressure provided thereby against the sidewall of the tube.

When it is time to withdraw the airway tube, a quick-release mechanism of the airway-tube holder can be actuated. This mechanism affirmatively disengages the female screw thread(s) from the thumb screw, with the result that the thumb screw and engagement arm can be rapidly retracted from the airway tube.

In various embodiments, the face plate, thumb screw, engagement arm, and quick-release mechanism are structurally implemented so as to provide one or more of the following features or characteristics, among any others:
provide coarse and fine adjustment of clamping pressure;
slide and/or thread the clamping head into or out of position;
a mechanical stop for preventing damage to the quick-release mechanism;
surfaces to prevent accidental actuation of the quick-release mechanism;
facilitate smooth movement of the thumb screw upon release from an airway tube;
improve contact with an airway tube;
increase thread grip between the thumb screw and female threads as the thumb screw tightens against an airway tube;
adaptations for stabilizing the engagement arm;
facilitate gliding motion of engagement arm; and
a syringe grip for improved ergonomics when pushing the thumb screw.

BRIEF DESCRIPTION OF THE DRAWINGS

The following is a brief description of the drawings, in which:

FIG. 1B depicts a perspective view of the airway-tube holder of FIG. 1.

DETAILED DESCRIPTION

Figure 1A:
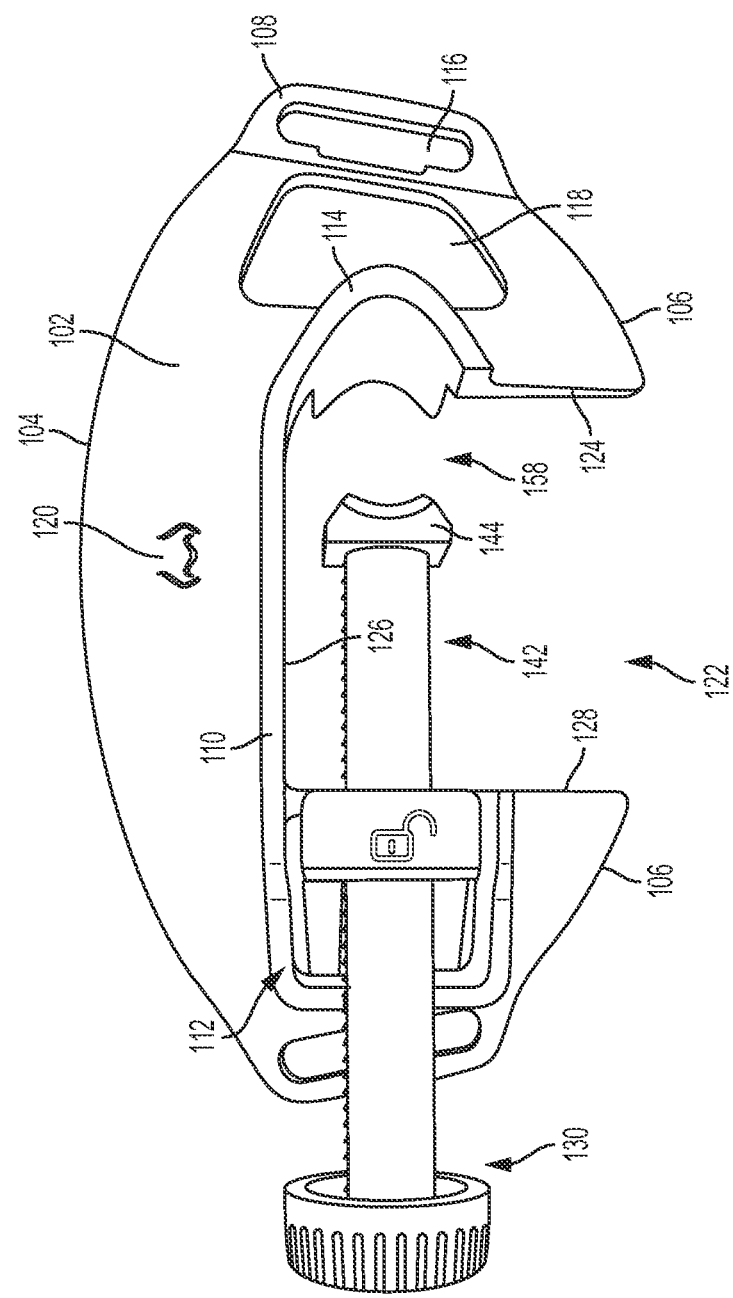
FIG. 1A depicts a front view of an airway-tube holder in accordance with the illustrative embodiment of the present invention.
Figure 2:
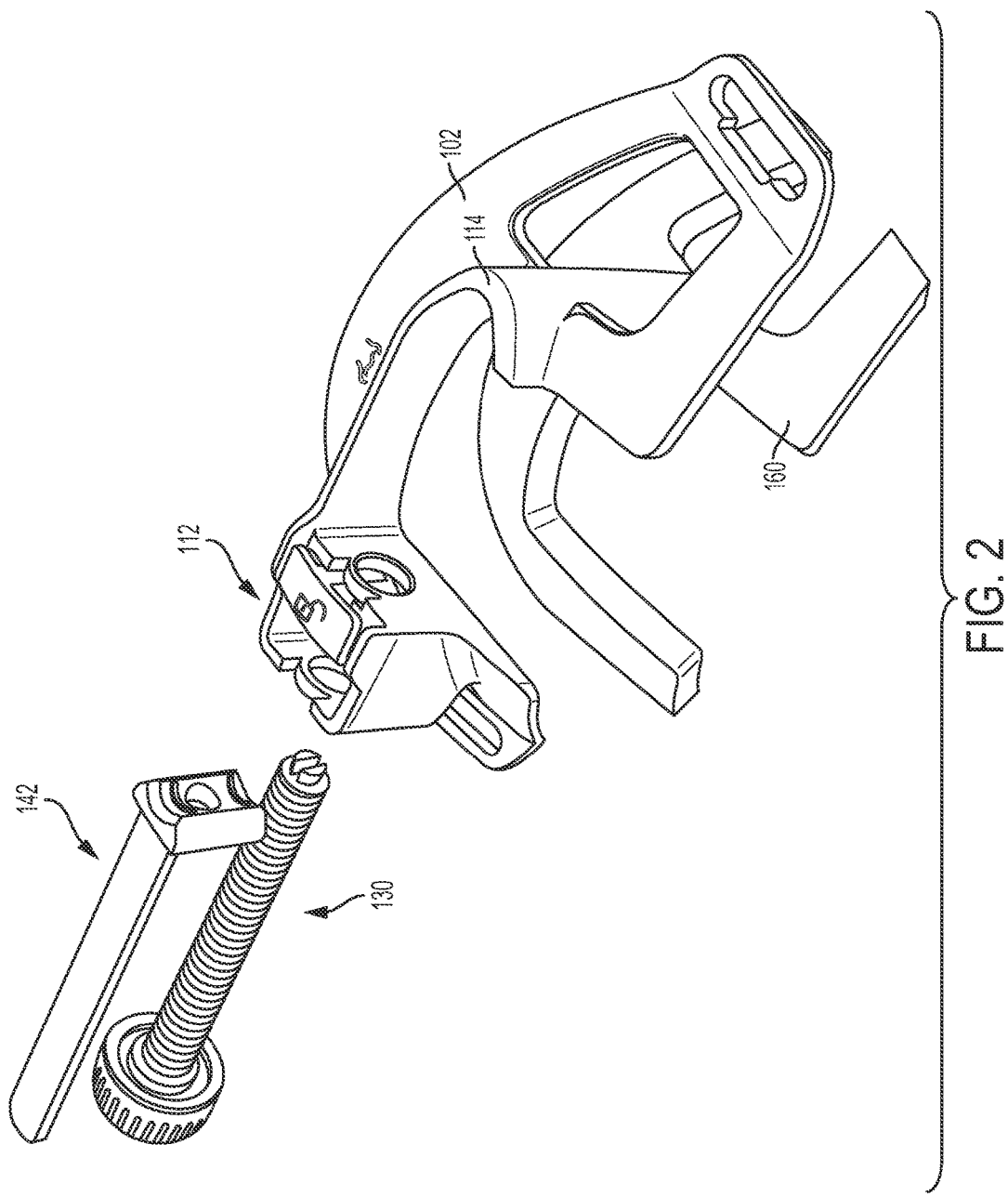
FIG. 2 depicts an "exploded" perspective view of the airway-tube holder of FIG. 1.

Reference to the "left" side or the "right" side of an article depicted in the accompanying drawings is to be understood as being from the "perspective" of the article, not the viewer. Reference to "up," "above," "down," or "below," in conjunction with a drawing refers to a viewer's perception of these directions when viewing the drawing, unless otherwise specified.

Overview of Airway-Tube Holder.

Referring now to FIGS. 1A, 1B, 2, and 3, in the illustrative embodiment, airway-tube holder 100 includes face plate 102, thumb screw 130, engagement arm 142, and padding 160.

Face plate 102 is dimensioned and configured to fit over a patient's oral cavity below the nose and above the chin. Face plate 102 has an arcuate form, wherein the patient-facing side (hereinafter "inner surface") of the face plate is curved to fit the contours of a patient's face in the aforementioned region of the face. The foregoing description serves as a minimum definition of the term "face plate," as used in this disclosure and the appended claims. That is, at a minimum, a face plate must exhibit the aforementioned configuration.

In the illustrative embodiment, the face plate has a roughly oblong shape defined by upper perimeter 104 and (partial) lower perimeter 106. The fit to a patient's face is also facilitated, in the illustrative embodiment, by forming face plate 102 from a lightweight, flexible, readily deformable material. Suitable materials include some thermoplastic materials, such as polypropylene, as well as others known to those skilled in the art.

In the illustrative embodiment, face plate 102 is monolithic in form (i.e., single-piece fabrication), but includes a variety of surface structural features. For example, face plate 102 includes a wall or flange 110 that extends outwardly, orthogonal to the outward-facing side (hereinafter "outer surface") of the face plate. Although an essentially continuous form in the illustrative embodiment, different portions of the wall are associated with different structures on face plate 102. For example, the right portion of wall 110 is a part of holding block 112 and the left portion of wall 110 defines tube-receiving surface 114. In the illustrative embodiment in which face plate 102 is monolithic, all structures formed therein/thereon comprise the same material (e.g., a flexible thermoplastic, etc.). In some other embodiments, face plate 102 is not a monolithic form; that is, one or more of the various structural features of face plate 102 can be integrated/attached thereto, by appropriate bonding techniques, etc. The various structures formed in/on face plate 102 are described in further detail below.

A salient feature of face plate 102 is channel 122, which has a roughly rectangular form and occupies the central portion of face plate 102. The channel extends from lower perimeter 106 of the face plate upwards about two-thirds of the way towards upper perimeter 104. Channel 122 is defined by: vertical edge 124 extending upwardly from left-side lower perimeter 106, tube-receiving surface 114 above vertical edge 124, horizontal upper edge 126 (which is the central portion of wall/flange 110), the left-most edge of holding block 112, and vertical edge 128, which is disposed below the holding block and terminates at right-side lower perimeter 106. Although it is desirable, as previously indicated, for face plate 102 to be flexible, in some embodiments, stiffening ribs are disposed on the inner surface of the portion of face plate 102 directly above channel 122 (see, e.g., FIG. 11C: stiffening ribs 1192). Since channel 122 effectively removes a large portion of face plate 102, the ribs provide additional structural reinforcement for the face plate.

Tube-receiving surface 114, which in the illustrative embodiment has a v-shaped form, extends channel 122 leftwards of vertical edge 124. Holding block 112 is disposed directly across channel 122 from tube-receiving surface 114. In the illustrative embodiment, the holding block receives thumb screw 130 and engagement arm 142, the latter including clamping head 144. As discussed later in this specification, the engagement arm and thumb screw are coupled to one another in such a way that the thumb screw has two degrees-of-freedom of motion (rotational and linear) yet the engagement arm has only one degree-of-freedom of motion (linear). The thumb screw is used to adjust the position the clamping head, so as to immobilize an airway tube or disengage therefrom.

By virtue of their relative positions, thumb screw 130, engagement arm 142, and tube-receiving surface 114 collectively define a clamp. And clamping head 144 and tube-receiving surface 114 collectively define an adjustable aperture 158 of the clamp that can immobilize an airway tube situated therein.

By way of explanation, in use of the device, an airway tube (not depicted) is first positioned in a patient's mouth and throat. Airway-tube holder 100 is then positioned on the patient's face below the nose and above the chin, with the airway tube sited in channel 122 close to tube-receiving surface 114. Alignment feature 120, which in the illustrative embodiment is an embossed image of a "nose," facilitates proper face-plate-to-face alignment. In particular, the face plate is placed so that alignment feature 120 aligns with the patient's nose. The inventors prefer to use an image of a nose, as opposed to language (i.e., "nose") or a non-descriptive alignment fiducial, to avoid language-comprehension issues and minimize any problems related to a caregiver's lack-of-familiarity with airway-tube holder 100.

An adjustable strap (not depicted), which is attached to slots 116, secures airway-tube holder 100 around the patient's neck. As discussed in further detail later in this specification, a caregiver advances thumb screw 130 and engagement arm 142 toward the airway tube until clamping head 144 abuts the sidewall of the airway tube, thereby immobilizing the airway tube. Access-way 118 enables a caregiver to access other tubes, etc., for example, extending from the patient's mouth.

Slots 116 for receiving the adjustable strap are disposed in flange-like regions 108, which are situated at the extreme left and right sides of face plate 102. The flanged regions deviate from the arcuate form of the main body of the face plate. That is, rather than following the inwardly curving profile of the main portion of face plate 102, flanges 108 bend "outward" (forward) such that they fall in a plane that is substantially parallel to thumb screw 130 and engagement arm 142. Within flanges 108, slots 116 are canted such that the lower portion of each slot is laterally inward of the upper portion thereof. The inventors observed that when strap-holding slots are oriented vertically (i.e., straight up and down) as in the prior art, the strap often slips (assuming it is not positioned above the ears), sliding downward from its initial position toward the patient's lower neck. This causes the strap to become slack with the result that the face plate will loosen. Although the airway tube will remain immobilized by whatever clamping mechanism is used in conjunction with the face plate, the tube will be free to move relative to the patient, which is unacceptable. To address this problem, and unlike the prior art, slots 116 are canted as described above. This facilitates initially siting the strap at a lower location about the neck, such that the likelihood of slippage is significantly reduced.

Padding 160 is disposed on the inner surface of face plate 102 to provide comfort for the patient. The padding is typically foam. The padding can be attached to face plate 102 via rivets (see, e.g., FIG. 11C: rivets 1194) that are integral thereto and extend from the inner surface thereof, such as disclosed in U.S. Pat. No. 8,360,063, which is incorporated by reference herein. Other methods for attaching the padding to the inner surface of the face plate, as will occur to those skilled in the art, can suitably be used.

Figure 3:
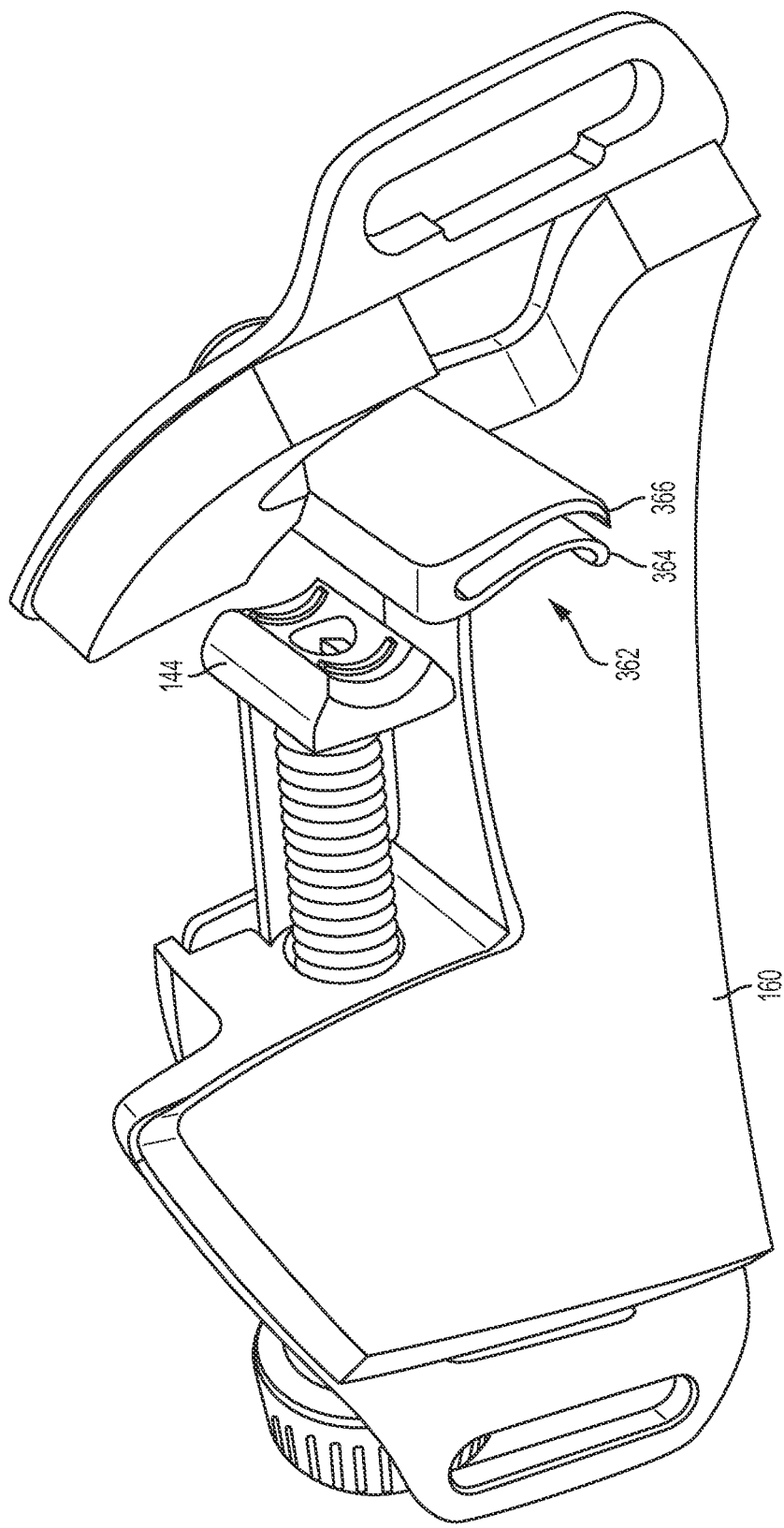
FIG. 3 depicts a perspective view of the patient-facing surfaces of the airway-tube holder of FIG. 1.

Airway-tube holder 100 also includes bite block 362, best viewed in FIG. 3. The bite block, which extends from the inner surface of face plate 102, is essentially an extension of, and has the same form as, tube-receiving surface 114. Bite block 362 has two spaced-apart walls 364 and 366. This arrangement imbues bite block 362 with flexibility sufficient to enable it to be grasped by a patient's teeth without affecting the airway tube mounted against it.

Figure 4:
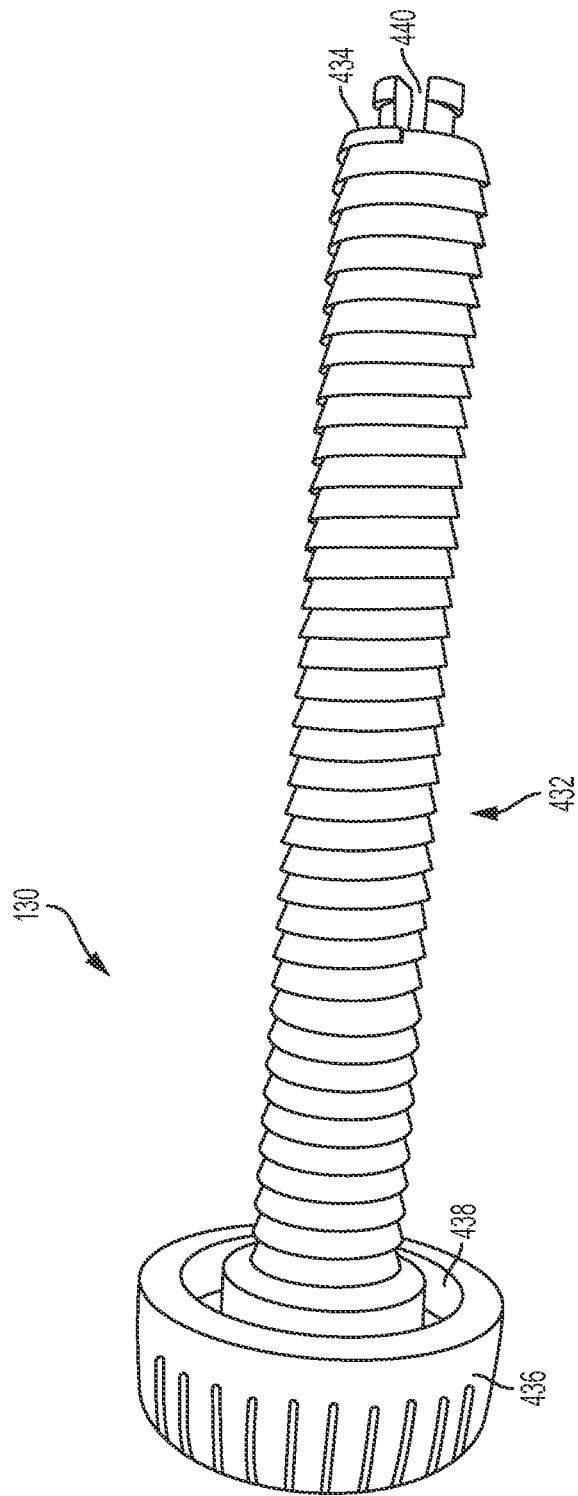
FIG. 4 depicts an embodiment of a thumbscrew of the airway-tube holder of FIG. 1.

FIG. 4 depicts thumb screw 130. The thumb screw includes head 436, threads 432, and coupler 440. In the illustrative embodiment, threads 432 have an asymmetric profile, unlike conventional screws.

As used in this disclosure and the appended claims, the term "asymmetric," when used to describe screw threads, means that the angle of inclination of one side of a thread is different than the angle of inclination of the other side of the same thread. As used in this disclosure and the appended claims, the term "leading side," when referencing thread direction, refers to the side of the thread that "leads" as thumb screw 130 is advanced toward tube-receiving surface 114. The term "trailing side," when referencing thread direction, refers to the side of the thread that "trails" as thumb screw 130 is advanced toward tube-receiving surface 114. These terms retain this meaning when the screw is advanced in the reverse direction. That is, even though the "trailing side" of the thread leads when the screw is moved away from tube-receiving surface 114, it maintains the designation "trailing side."

In the illustrative embodiment, head 436 is knurled. The head includes retaining groove 438, which has an annular form and receives end 556 of stem 550 (see FIG. 5) of engagement arm 142. Coupler 440, which is co-axial with threads 432, extends from forward surface 434 of thumb screw 130. In the illustrative embodiment, coupler 440 is implemented as two spaced-apart members that are enlarged at their free ends. The enlargement creates a shoulder on each member that functions as a catch when forced through an appropriately sized opening.

As will be appreciated by those skilled in the art, a different style of head (e.g., spade, wing, etc.) can be used in conjunction with thumb screw 130, as long as it includes (for airway-tube holder 100) a groove like groove 438 that receives the end of stem 550. The thumb screw is made from a lightweight, relatively low-cost material that is robust enough for use in low- to medium-stress components. Suitable materials include some thermoplastics, such as various nylons, among other materials known to those skilled in the art.

As described later in conjunction with FIGS. 6, 7, and 8, as facilitated (but not necessitated) by its asymmetric threads, thumb screw 130 is slideable along one direction and locks in the other direction.

Figure 5:
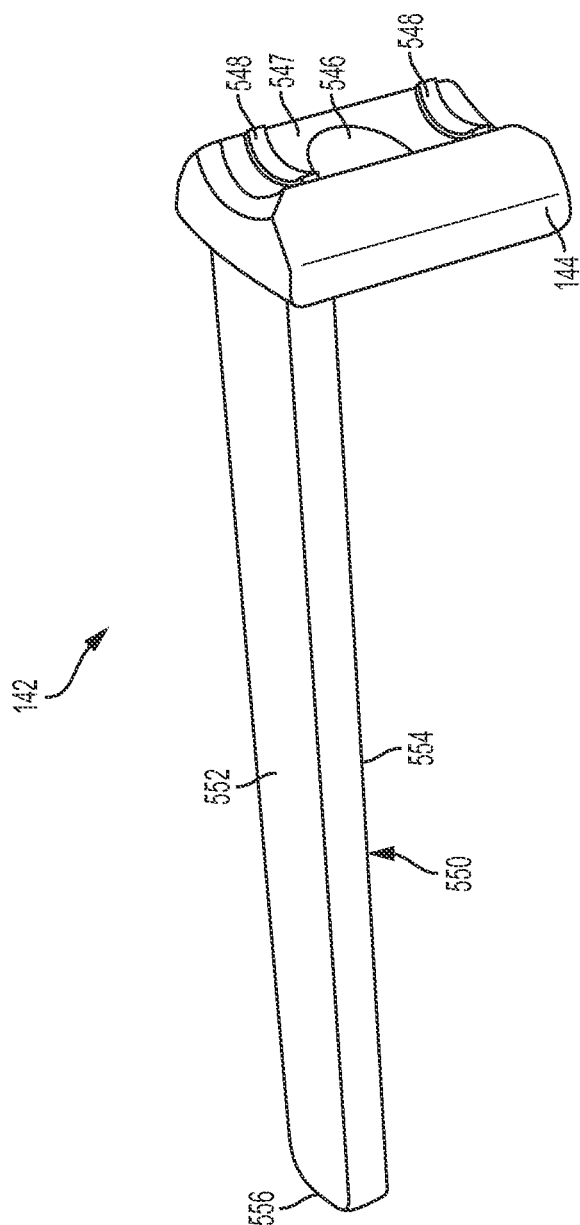
FIG. 5 depicts an embodiment of an engagement arm of the airway-tube holder of FIG. 1.

FIG. 5 depicts engagement arm 142. The engagement arm includes stem 550 and clamping head 144 disposed at one end thereof. Upper surface 552 of the stem has a convex profile and lower surface 554 thereof has a concave profile. This facilitates coupling end 556 of stem 552 to retaining groove 438 (see, e.g., FIG. 1B) in the head of thumb screw 130. Surface 547 of clamping head 144 is curved to facilitate engagement with the sidewall of an airway tube. In the illustrative embodiment, ribs 548 are disposed on surface 547. As compared to a relatively larger planar surface such as surface 547, ribs 548, which in the illustrative embodiment have an arcuate shape matching the curve of surface 547, ensure positive contact with the sidewall of an airway tube and enable more pressure to be applied thereto. Opening 546 in clamping head 144 receives coupler 440 of thumb screw 130, snapping the two parts together. In some embodiments, all features of the engagement arm are made from the same material as thumb screw 130.

Holding Block.

Figure 6A:
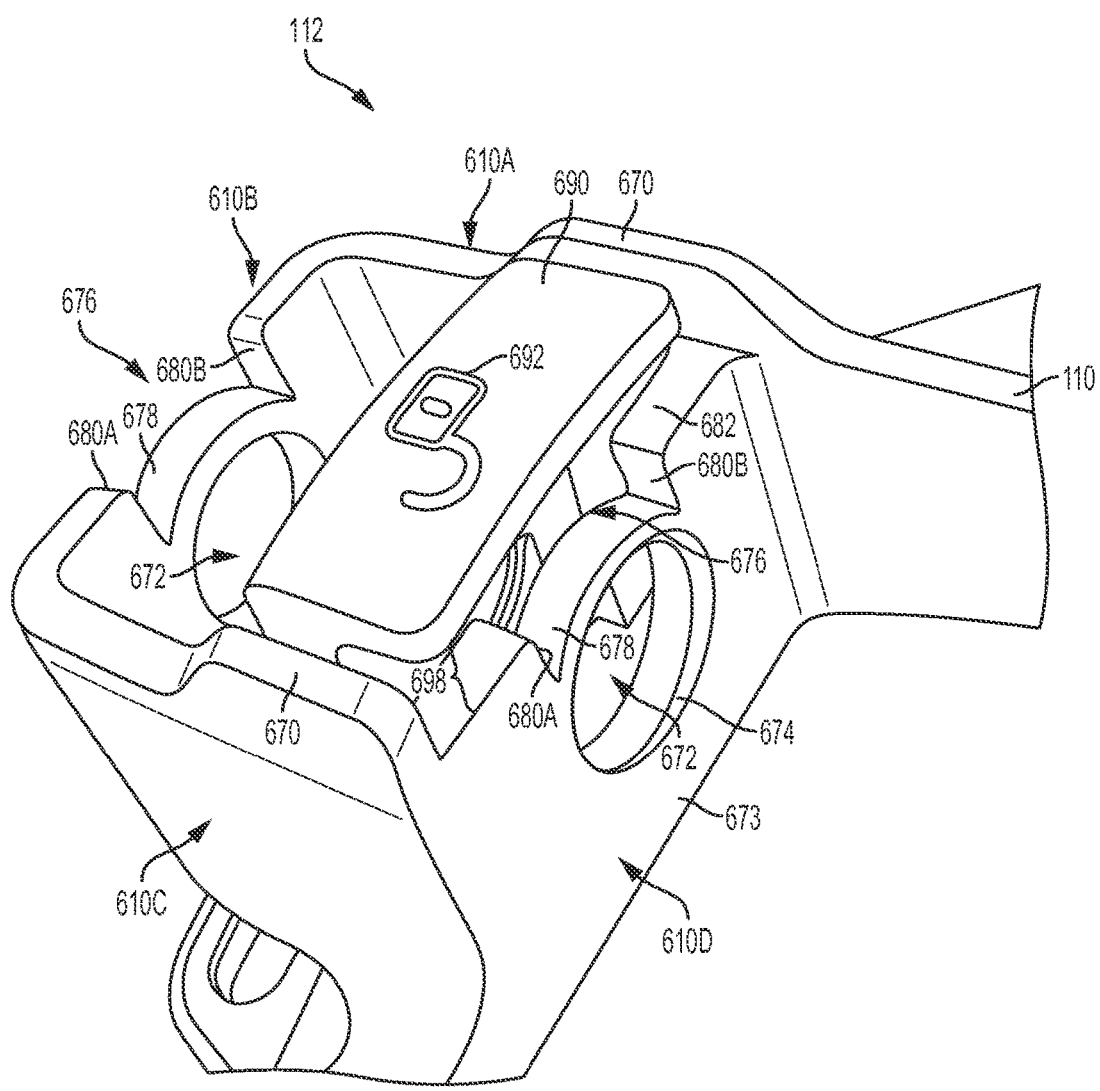
FIG. 6A depicts a perspective view of a holding block of the airway-tube holder of FIG. 1.
Figure 6B:
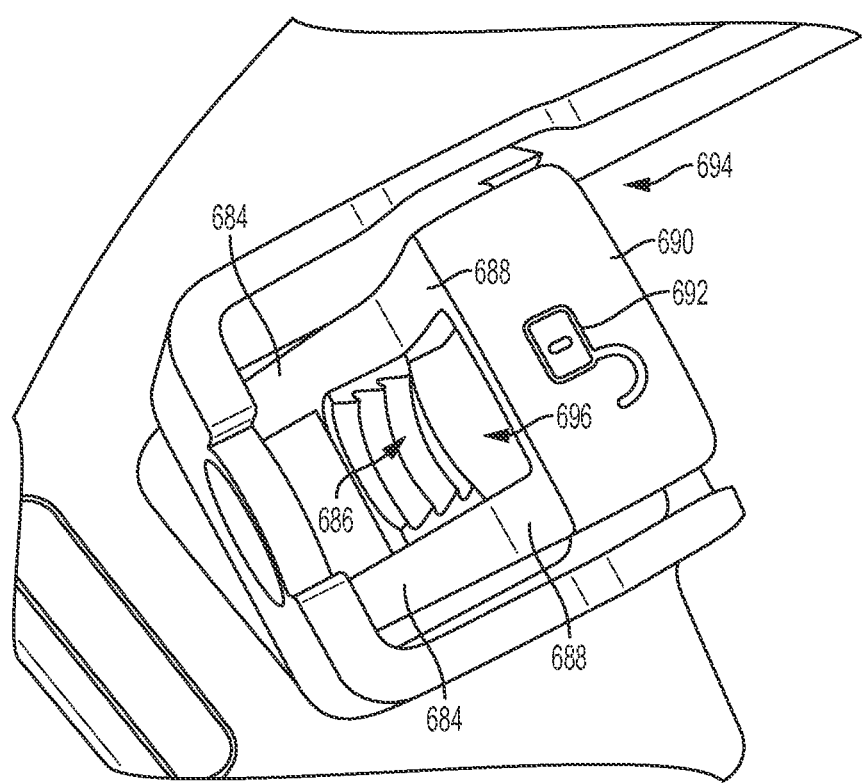
FIG. 6B depicts a top perspective view of the holding block of FIG. 6A.
Figure 7:
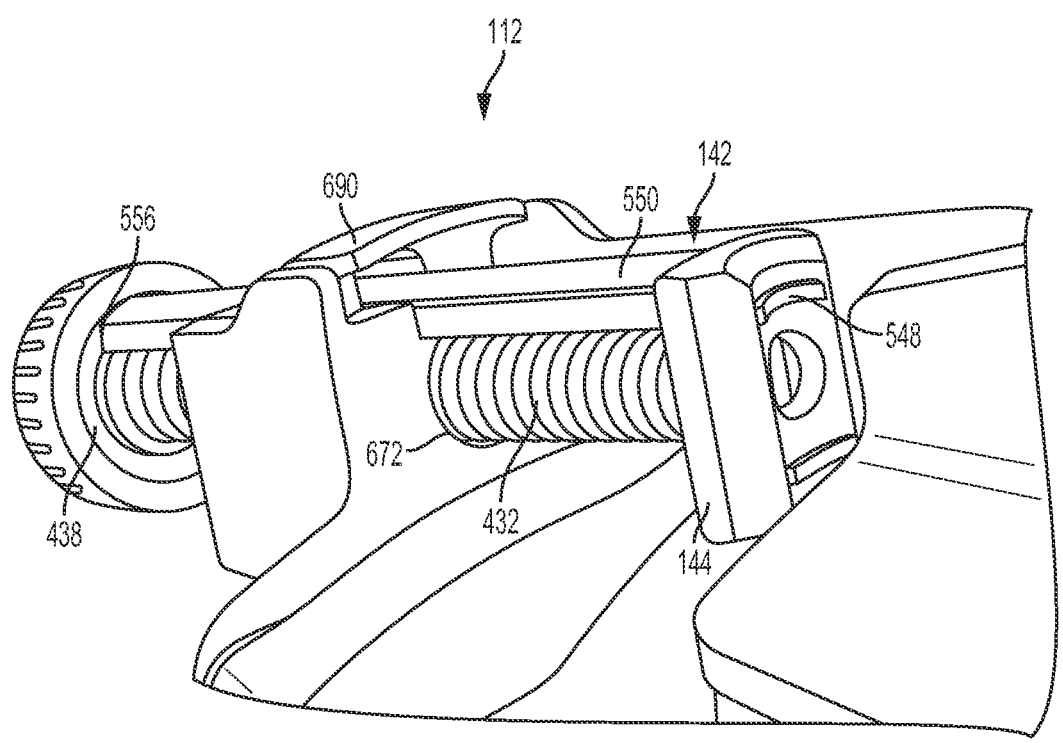
FIG. 7 depicts the thumb screw of FIG. 4 and engagement arm of FIG. 5 coupled to the holding block of FIG. 6.

FIGS. 6A, 6B, and 7 provide further detail of holding block 112 and the manner in which thumb screw 130 and engagement arm 142 cooperate therewith. In conjunction with FIGS. 6A, 6B, and 7, the terms "above," "higher," or "outwardly of" mean "further from the surface of face plate 102." Conversely, the terms "below," "lower," or "inwardly of" mean "closer to the surface of face plate 102."

Referring now to FIG. 6A, in the illustrative embodiment, holding block 112 has an approximately square perimeter, as defined by walls 610A, 610B, 610C, and 610D (collectively "walls 610"). These walls are specific segments of wall/flange 110. Walls 610A and 610C each have raised guard portion 670. These guard portions reduce the likelihood of inadvertent contact with plate member 690, the implications of which are discussed further below.

Walls 610B and 610D each include openings 672. In the illustrative embodiment, these openings are circular and are dimensioned to receive thumb screw 130. Groove 676 is disposed in walls 610B and 610D above opening 672 therein. Each groove 676 is defined by bottom surface 678 and sidewalls 680A and 680B. Grooves 676 are dimensioned and arranged to receive stem 550 of engagement arm 142. As a consequence, the separation between opposing sidewalls 680A and 680B of each groove is slightly greater than the width of stem 550. Furthermore, since lower surface 554 of stem 550 has a concave shape, bottom surface 678 of each groove has a complementary convex form. This facilitates smooth, gliding movement of stem 550 of engagement arm 142 within grooves 676.

With reference now to FIG. 6B, in some embodiments, two spaced-apart arms 684 depend from wall 610B proximal to the base thereof (i.e., relatively closer to the surface of face plate 102). Arms 684 are angled outwardly and are capable of flexing, predominantly at the intersection with wall 610B. Partial female threads 686 span the gap between spaced-apart arms 684.

In the illustrative embodiment, partial female threads 686 comprise three partial threads, which provides sufficient thread grip, when required, in conjunction with thumb-screw threads 432, preferably asymmetric, with they engage. In some other embodiments, female threads 686 comprise one or two partial threads, and in yet some further embodiments, more than three partial threads are used. Using several partial threads, as opposed to a single thread, distributes the force applied by the thumb screw 130, permitting a less durable plastic to be used for the female threads.

As the descriptor "partial" indicates, female threads 686 are not "full" threads in the sense that they do not extend for 360-degrees of arc. As used in this description and appended claims, the term "partial", when used to reference a male or female screw thread, means a segment of thread that extends for less than 360-degrees of arc. In other words, the term "partial" does not refer to the number of threads, but rather the circumferential extent of a thread. The significance of the use of partial female threads 686 is discussed in further detail later in this disclosure.

At the free end of each arm 684, arms 688 extend outwardly, rising above upper surface 682 of wall 610D. Plate member 690 is disposed on top of arms 688. Opening 696 is formed between arms 688 and below plate member 690. This opening, in conjunction with openings 672, permits passage of thumb screw 130 through holding block 112.

Gap 698 (FIG. 6A) is defined between upper surface 682 of wall 610D and the lower surface of plate member 690. As discussed further below, arms 684, arms 688, and plate member 690 collectively function as quick-release mechanism 694 for decoupling threads 432 of thumb screw 130 from partial female threads 686. Icon 692, which in the illustrative embodiment is embossed on the upper surface of plate member 690, is a pictorial representation of an open "lock." This is intended to indicate to a user that pressing plate member 690 will actuate the quick-release mechanism.

Referring now to FIGS. 4, 5, 6A, 6B, and 7, to assemble airway-tube holder 100, thumb screw 130 is inserted through opening 672 in wall 610B, through opening 696 in quick-release mechanism 694, and through opening 672 in wall 610D. End 556 of stem 550 of engagement arm 142 is positioned in groove 676 of wall 610D and advanced across holding block 112 where it is received by groove 676 in wall 610B.

End 556 of stem 550 is advanced until it is received by annular retaining groove 438 in head 436 of the thumb screw. At the same time, opening 546 in clamp head 144 of the engagement arm receives coupler 440 (of thumb screw 130) to fixedly couple engagement arm 142 to thumb screw 130. It is to be understood that the fabrication process described above can be reversed; that is, engagement arm 142 can be inserted into holding block 112 before thumb screw 130.

Engagement of Thumb Screw to Partial Female Threads.

As previously described, in the illustrative embodiment, threads 432 of thumb screw 130 have an asymmetric profile and partial female threads 686 have a complementary (opposite) asymmetric thread profile. Having an asymmetric profile of the indicated directionality (i.e., the leading side of the thread tapers from narrow to wider) facilitates pushing thumb screw 130 toward tube-receiving surface 114 with little resistance from partial female threads 686. Once in abutting or near abutting relation with the sidewall of an airway tube, a user can turn (i.e., thread) rather than push thumb screw 130, thereby fine-tuning the clamping force applied to an airway tube.

The asymmetry of threads 432 of thumb screw 130 facilitate the bi-functionality of the thumb screw (i.e., capable of sliding movement or threading movement) and improve its performance in that regard. In some other embodiments, however, thumb-screw threads 432 are symmetric and can still be slid over partial female threads 686 (which are symmetric in embodiments in which the thumb-screw threads are symmetric) as a consequence of the manner in which the partial female threads are supported.

A particularly advantageous characteristic of the illustrative embodiment is that once thumb screw 130 meets resistance, such as when clamping head 144 of engagement device 142 presses against the sidewall of an airway tube, the thread grip increases as the thumb screw is incrementally tightened.

This is a result, in the illustrative embodiment, of a "vertical" offset and a "horizontal" offset between the point at which arms 684 (which support partial female threads 686) are supported and the point of engagement between the male and female threads. This phenomenon is discussed further below in conjunction with FIGS. 8A and 8B, which depict force diagrams for two arrangements. For the analysis depicted in these Figures, it is assumed that arms 884A and 884B are rigid and that all bending occurs at elastic-"hinge" point 802, wherein bending the arms at elastic-hinge point 802 results in a restoring torque.

Figure 8A:
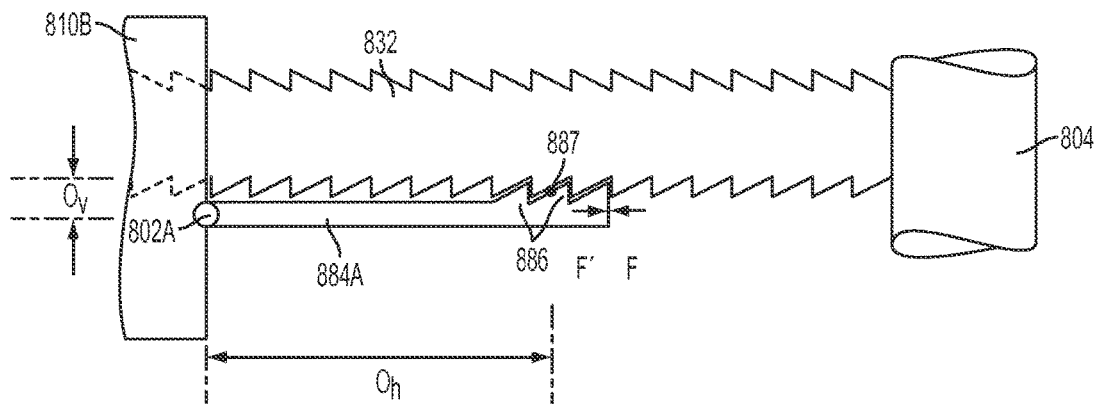
FIGS. 8A and 8B depict force diagrams.

FIG. 8A depicts an arrangement in which there is a non-trivial "horizontal" offset $O_h$, but essentially no "vertical" offset $O_v$ between elastic-hinge point 802A and the point at which screw threads 832 and partial female threads 886 engage one another.

The arrangement depicted in FIG. 8A includes wall 810B, which supports, at elastic-hinge point 802A, arm 884A. The arm supports partial female threads 886. A screw having threads 832, which are asymmetric in this embodiment, passes through an opening in wall 810B and engages the female threads 886. The screw abuts airway tube 804.

The force applied by the screw on arm 884A is F, and the counterforce from the arm 884A is F'. Both force F and counterforce F' are horizontal; that is, these forces have a "zero angle" with respect to one another since there is no vertical offset $O_v$ between the elastic-hinge point 802A and the point at which the male and female threads engage one another. (Although FIG. 8A actually shows a small vertical offset $O_v$, for simplicity, the force analysis presented below assumes that there is no vertical offset.) As such, the vertical force from arm 884A to screw threads 832 (which is a function of the amount of upward pretension provided to arm 884A) is constant. As a consequence, the thread grip is dependent upon a sufficiently strong pretension in arm 884A.

Figure 8B:
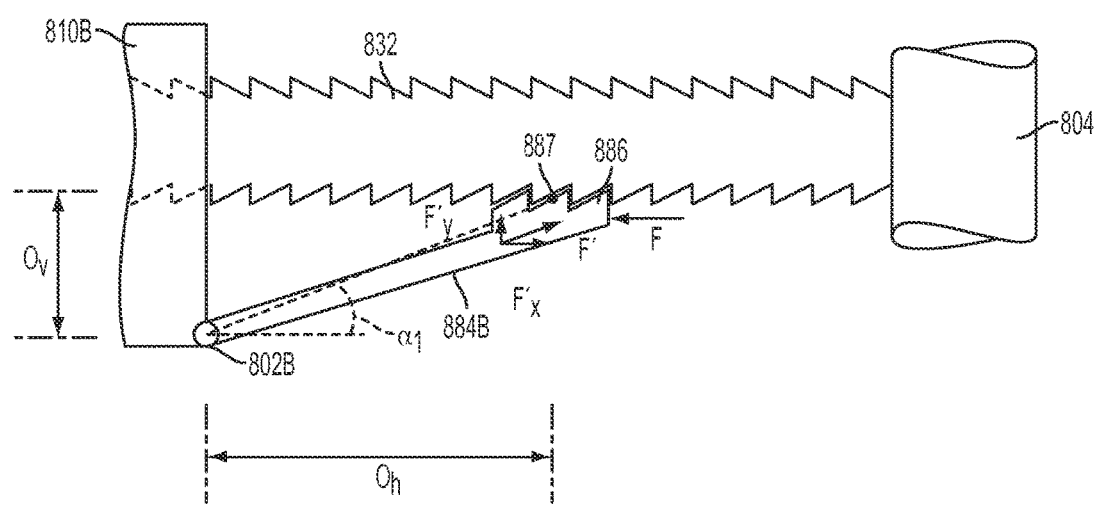

FIG. 8B depicts an arrangement in which, in addition to a horizontal offset $O_h$, there is a non-trivial vertical offset $O_v$ between elastic-hinge point 802B and the point at which the male and female threads engage one another (hereinafter the "thread-engagement point").

The arrangement depicted in FIG. 8B includes wall 810B, which supports, at elastic hinge 802B, arm 884B. The arm supports partial female threads 886. A screw having threads 832, which are asymmetric in this embodiment, passes through an opening in wall 810B and engages the female threads 886. The screw abuts airway tube 804.

The force analysis in this example, which shows a significant vertical offset $O_v$ between the arm's elastic-hinge point 802B and thread-engagement point 887, is different from that of the zero-offset case depicted in FIG. 8A. As depicted in FIG. 8B, although force F applied by the screw is horizontal, the counterforce F' from arm 884B is not horizontal; that is, it is directed at a non-zero angle with respect thereto consistent with angle $\alpha_1$ (based on vertical offset $O_v$ and horizontal offset $O_h$) between elastic hinge point 802B and thread engagement point 887. For purposes of illustration/analysis, thread-engagement point 887 is considered to be the intersection of the vertical midpoint of the threads and horizontal midpoint of the threads.

Counterforce F' can be resolved into two scalar components $F'_x$ and $F'_y$. Vertical component $F'_y$ (and the horizontal component $F'_x$) of the counterforce increases with an increase in force F. As a consequence, as the screw is tightened against airway tube 804, the thread grip (which results from the vertical counterforce) increases. Conversely, in the absence of a resistance such as that presented by airway tube 804, the screw can be pushed over the partial female threads, even though the male and female threads are initially engaged.

It will be appreciated by those skilled in the art that even if the arms that support the partial female threads are not rigid, such that bending occurs across the length of the arm (not solely at elastic hinge point 802), thread grip will increase per the foregoing analysis.

Regarding thread asymmetry/symmetry, it is notable that greater wear is expected to be experienced by both the male and female threads due to repeated pushing of the thumb screw for a thread profile that is relatively less asymmetric (relatively more symmetric) than in the illustrative embodiment. As previously indicated, in the illustrative embodiment, to facilitate "sliding" of thumb screw 130 towards tube-receiving surface 114, the leading side of the threads tapers from narrow (front edge) to wide (back edge).

Figure 8C:
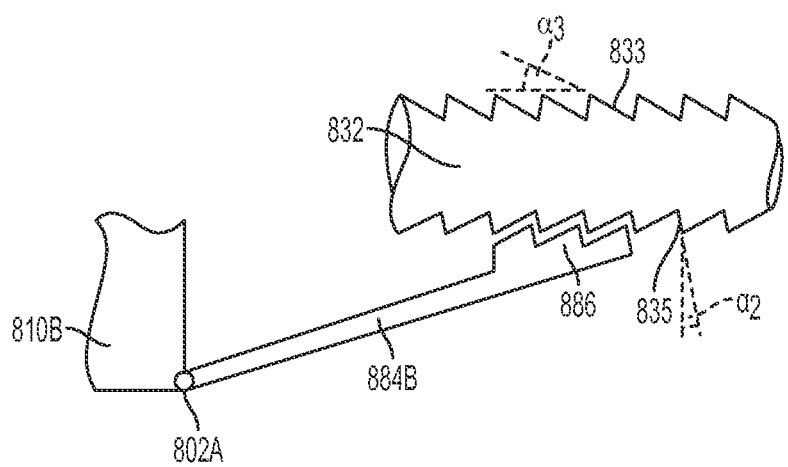
FIG. 8C depict details about the trailing and leading surface of the thumbscrew threads.

Referring now to FIG. 8C, which depicts a partial view of the arrangement depicted in FIG. 8B, angle-of-inclination $\alpha_3$ of leading edge 833 of the thumb-screw threads 832 is in a range of about 5 to about 50 degrees, more preferably in a range of about 10 to 40 degrees, and most preferably within a range of about 15 to 30 degrees. For a given crest height, as angle-of-inclination $\alpha_3$ decreases, the length of the thread increases. As angle-of-inclination $\alpha_3$ increases, more noise is generated when the thumb screw is slid past the partial female threads.

Angle-of-inclination $\alpha_2$ of trailing side 833 of the thumb screw's threads 832 is typically in a range of about 0 to 15 degrees (i.e., wherein 0 degrees is "vertical" in FIG. 8C).

Angle $\alpha_1$ (FIG. 8B) of arm 884B should be greater than angle-of-inclination $\alpha_2$ so that the ability to immobilize the thumb screw is not dependent on the friction within the threads.

It will be appreciated by those skilled in the art that for the scenario depicted in FIG. 8B as well as in the illustrative embodiment, the vertical movement of the screw must be limited. That is, clearance between the outermost diameter of thumb-screw threads 432 (measured at the crest of a thread) and opening 672 must be limited to amount that is related to the pre-tension (i.e., upward bias) of the arms that support the female threads (i.e., arms 684 in the illustrative embodiment). In some embodiments, the gap is limited to 0.1 millimeters (mm). If the vertical tolerance for movement of the screw is greater than the pretension in the arms and the thread height, the arms will not be able to create any grip tension on the screw threads, such that unintentional sliding of the screw over the female threads is likely to occur. In accordance with embodiments of the invention, the only way to achieve no grip and no thread tension is to use the quick release mechanism.

Quick Release Mechanism.

The pressure applied against an airway tube by engagement arm 142/thumb screw 130 can be released in either of two ways. A caregiver can simply "un-screw" thumb screw 130, turning head 436 counterclockwise. A much quicker way to release the engagement arm and thumb screw is to actuate quick-release mechanism 694.

Referring again to FIGS. 6A and 6B, as previously mentioned, arms 684, arms 688, and plate member 690 collectively function as quick-release mechanism 694 for decoupling threads 432 of thumb screw 130 from partial female threads 686. The quick-release mechanism is actuated by pressing plate member 690. The plate member is coupled, via arms 688, to arms 684 that support partial female threads 686. Pressing plate member 690 therefore causes threads 686 to move downward. Since thumb screw 130 is constrained to lateral movement via openings 672, the downward movement of partial female threads 686 disengages them from threads 432 of thumb screw 130. Once the female threads are disengaged, thumb screw 130 and engagement arm 142 can be slid away from the formerly immobilized airway tube.

As a consequence of the directionality of asymmetric threads 432, in the case of movement away from an airway tube, the thumb screw cannot simply be slid over the female threads as when the screw is being moved towards a tube. This is because the threads will present an edge with a steep angle (i.e., in the range of about 75 to 90 degrees) to asymmetric partial female threads 686, which would substantially hinder or prevent movement of thumb screw 130 unless quick release mechanism 694 is actuated.

As best seen in FIG. 6B, downward movement of plate member 690 is enabled by gap 698 between bottom surface of the plate member and top surface 682 of wall 610D. Top surface 682 thus functions as a mechanical "stop" to prevent excessive downward movement of arms 684. Repeated excessive movement could cause arms 684 to fail.

To implement the quick-release feature in a straightforward, uncomplicated manner, the female threads cannot fully surround the male threads 432. For use with the illustrative embodiment, the arc length of female threads 686 should be less than 180 degrees, and preferably about 90 degrees (i.e., one-quarter of the way around a circle). Otherwise, the female threads would not fully disengage from the male threads.

The maximum permitted arc length is based on the dimensions of the thread as well as the distance that female threads 686 can move away from male threads 432. Based on these considerations, one skilled in the art will be able to calculate the maximum allowable length of arc for the female threads. Alternatively, simple experimentation can be used to determine a length of arc that provides the requisite clearance.

In the illustrative embodiment, the distance that female threads 686 can move away from the male threads is limited by the size of gap 698 between the bottom surface of plate member 690 and surface 682 of wall 610D. And the size of gap 698 is selected to ensure that thread-supporting arms 684 do not fail by exceeding their flexural limitations. In light of the present teachings, those skilled in art will know how to balance these factors when developing a design for partial female threads 686 and quick-release mechanism 694.

To facilitate smooth sliding movement of thumb screw 130 away from an airway tube, at least a portion of the perimeter of opening 672 in wall 610D at surface 673 includes chamfer 674.

First Alternative Embodiment

Figure 11A:
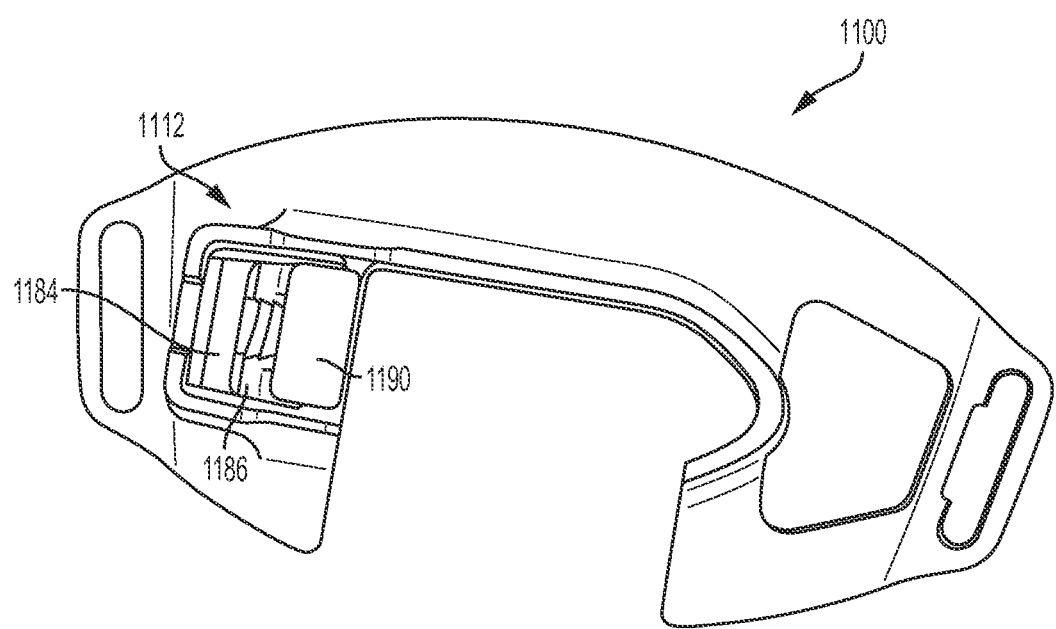
FIG. 11A depicts a front view of a first alternative embodiment of the airway-tube holder of FIG. 1.
Figure 11B:
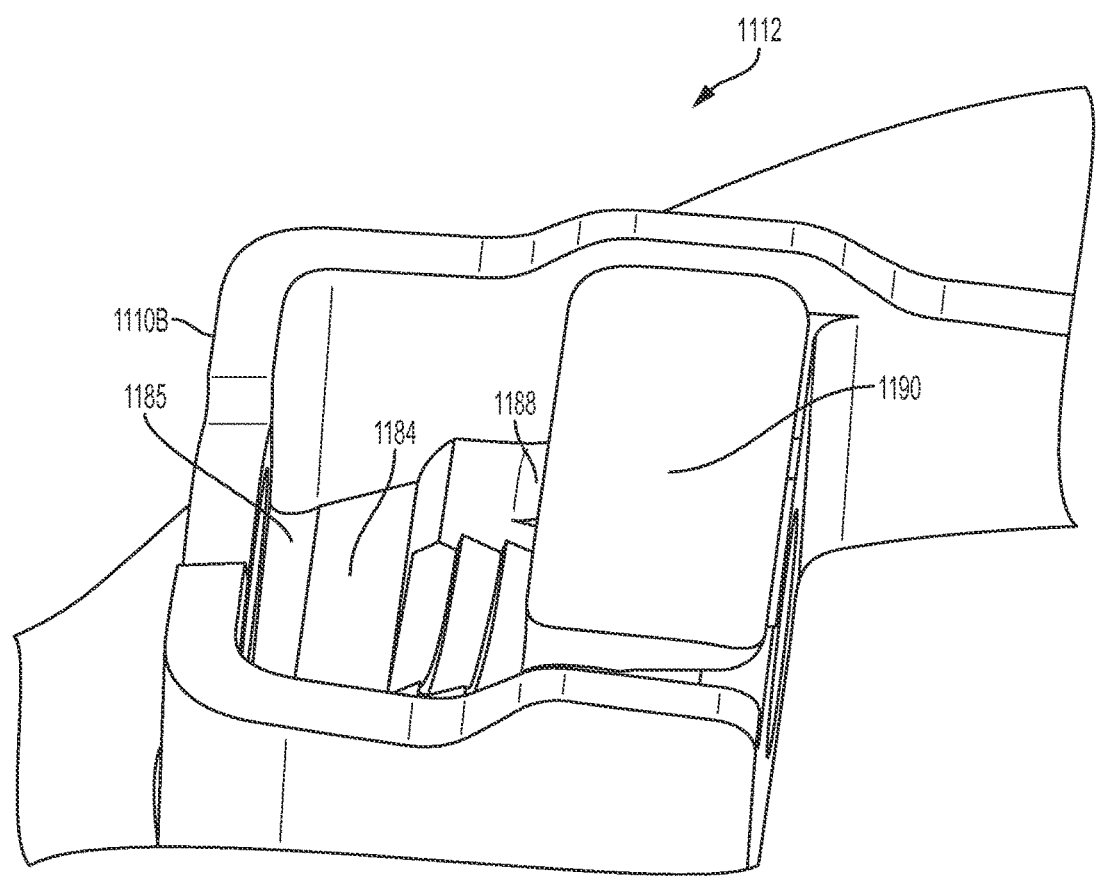
FIG. 11B depicts a top perspective view of the holding block of the airway tube holder of FIG. 11A.
Figure 11C:
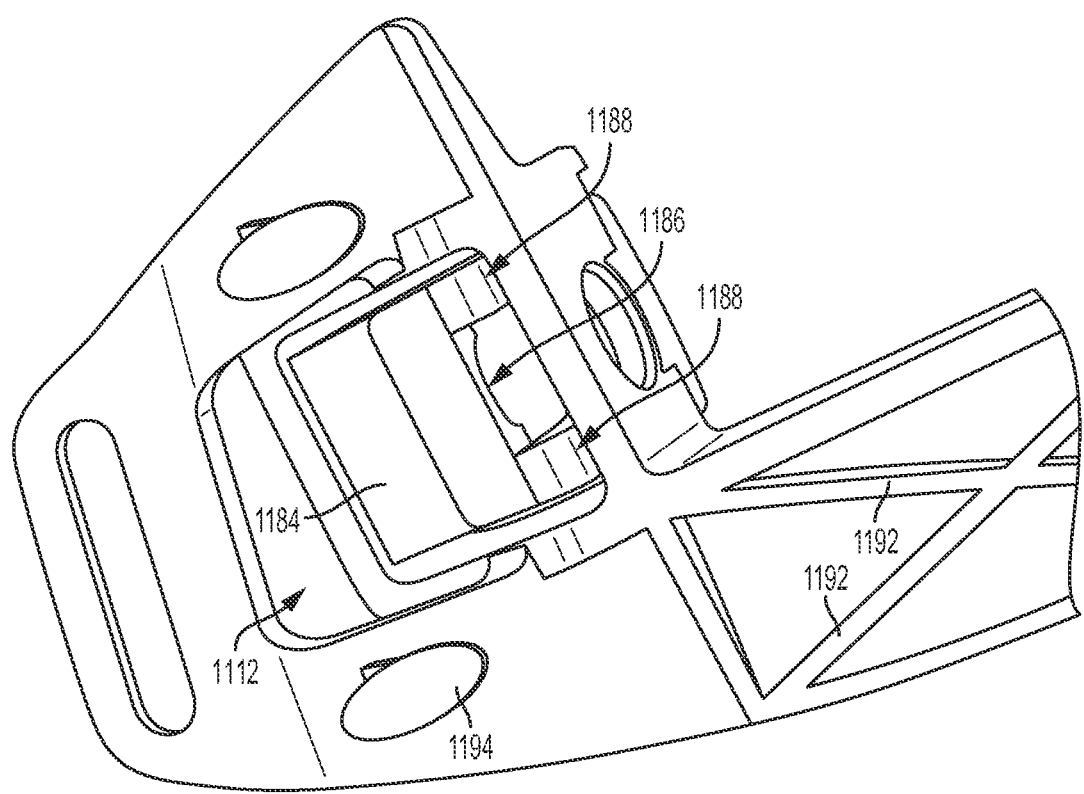
FIG. 11C depicts a bottom perspective view of the holding block of the airway tube holder of FIG. 11A.

FIGS. 11A through 11C depict airway-tube holder 1100. This embodiment of the airway-tube holder differs from airway-tube holder 100 in the particulars of the design of the holding block, but is otherwise identical. Specifically, in airway-tube holder 1100, holding block 1112 includes only a single arm—arm 1184—for supporting partial female threads 1186. As in the previous embodiments, two arms 1188 are used to support the plate member 1190.

In this embodiment, arm 1184 includes a physical adaptation that promotes flexing at a single location on the arm; that is, the arm behaves as a rigid member and the physical adaptation emulates the elastic hinge with a restoring torque upon bending, as discussed in FIGS. 8A-8B. In the illustrative embodiment, the physical adaptation is a thinned region 1185 of arm 1184. The arm is more likely to flex in thinned region 1185 than elsewhere along the arm. This is arrangement is similar to a "living" hinge, wherein a material is thinned or cut to allow rigid pieces to bend along the line of the "hinge." However, living hinges typically do not provide a restoring torque upon bending, wherein arm 1184 with thinned region 1185 will provide such a restoring torque. For use in this disclosure and the appended claims, the term "elastic living hinge" is used to refer to a living hinge that provides a restoring torque. Thinned region 1185 is located near the junction of arm 1184 with wall 1110B. In some other embodiments, other arrangements are used to emulate the functionality of a hinge to promote flexing of arm 1184 near wall 1110B.

Second Alternative Embodiment

FIGS. 9A, 9B, 10A and 10B depict airway-tube holder 900, which is a first alternative embodiment of airway-tube holder 100. The primary distinctions between airway-tube holder 900 and airway-tube holder 100 pertain to the design of the holding block, quick-release mechanism, and engagement arm.

Figure 9A:
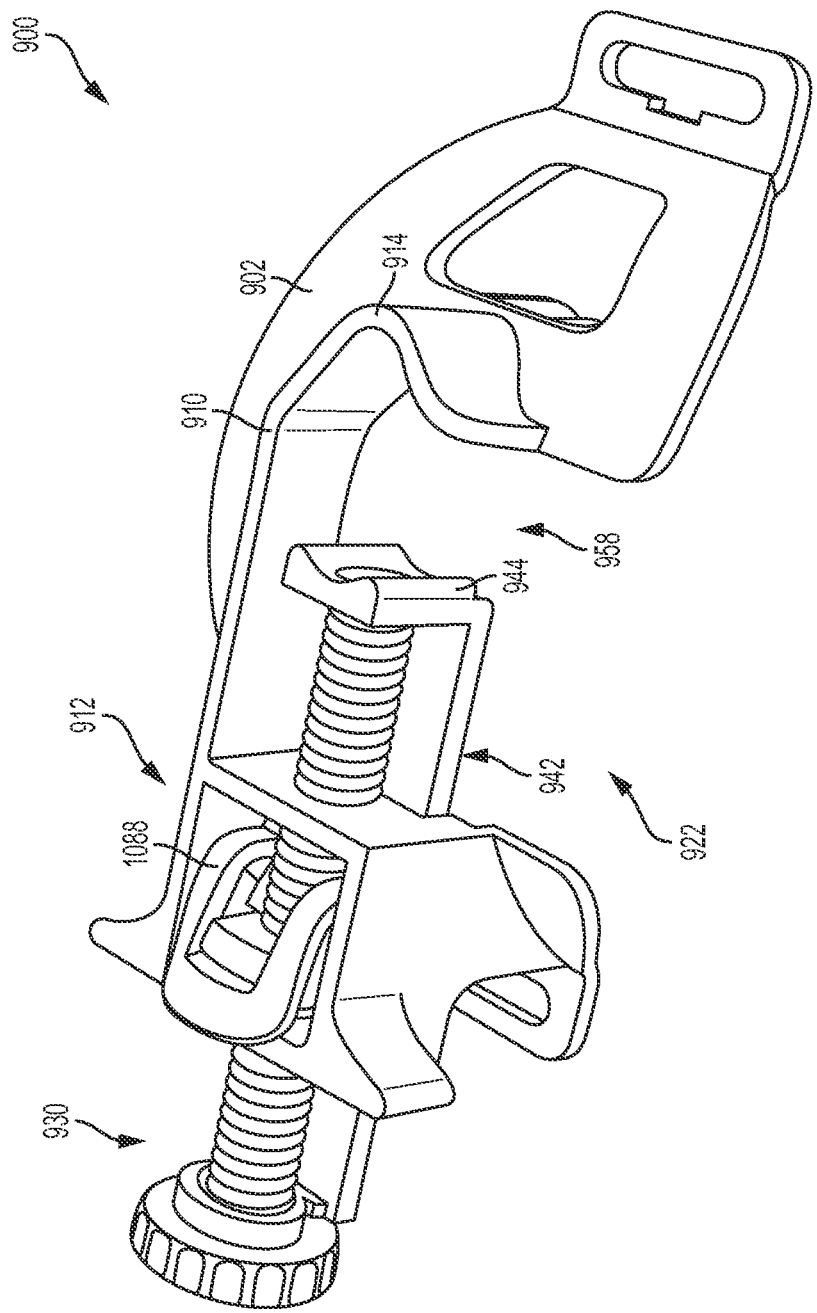
FIG. 9A depicts a perspective view of a second alternative embodiment of the airway-tube holder of FIG. 1.
Figure 9B:
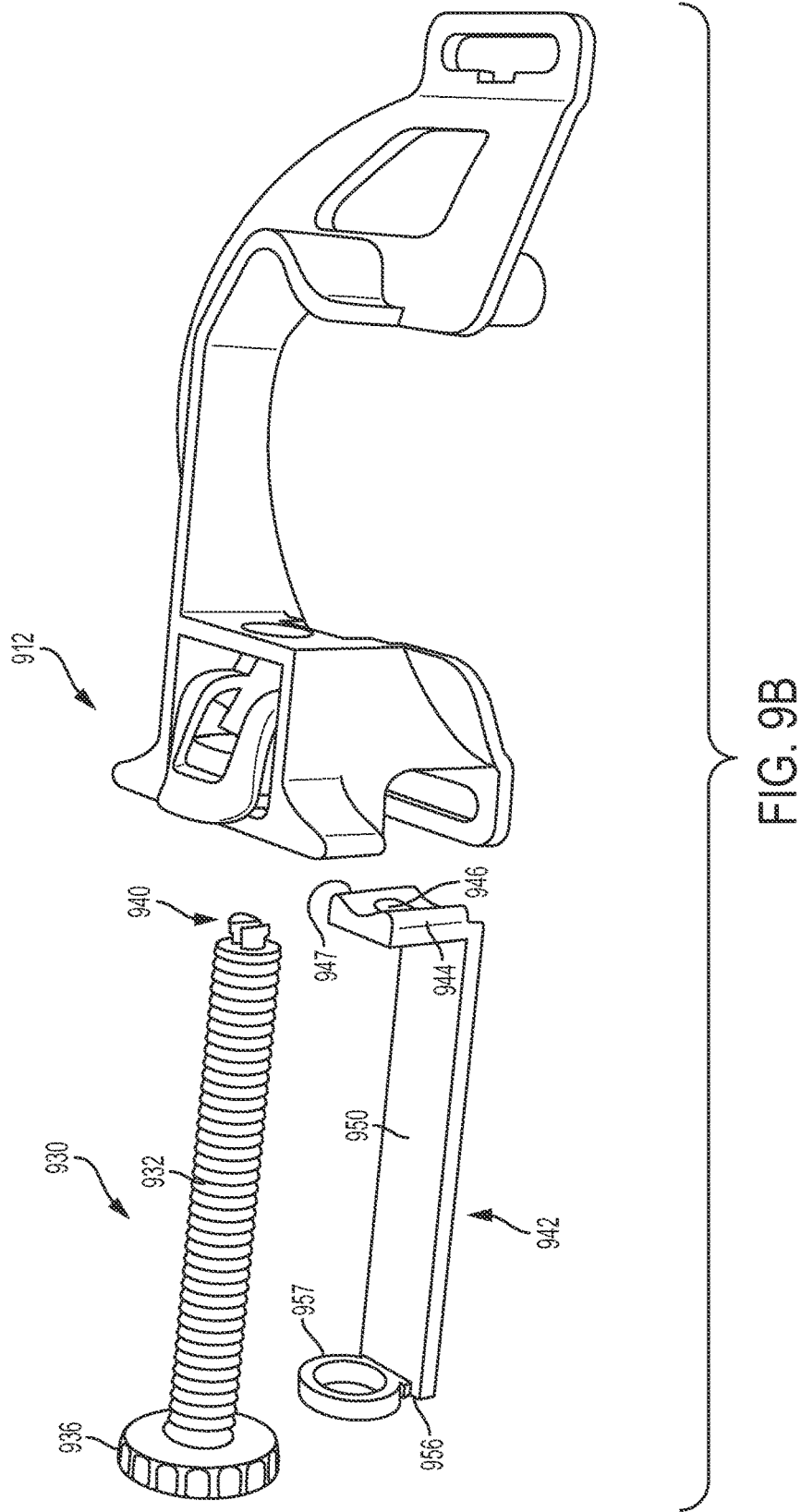
FIG. 9B depicts an exploded view of a portion of the airway-tube holder of FIG. 9A.

Referring now to FIGS. 9A and 9B, airway-tube holder 900 includes face plate 902, thumb screw 930, and engagement arm 942. Padding, not depicted, is disposed on the inner (patient-facing) surface of face plate 902. The shape of face plate 902 is similar to that of face plate 102.

Like face plate 102, face plate 902 includes a wall or flange 910 that extends outwardly, orthogonal to the outer surface of the face plate. Although an essentially continuous form, different portions of wall 910 are associated with different structures on face plate 902. The right portion of wall 910 forms a part of holding block 912 and the left portion of wall 110 defines tube-receiving surface 914.

The central portion of face plate 902 is occupied by channel 922, which has a roughly rectangular form like channel 122 of face plate 102. Tube-receiving surface 914, which has a v-shaped form, defines a portion of the left side of channel 922. Holding block 912 is disposed directly across channel 922 from tube-receiving surface 914. The holding block receives thumb screw 930 and engagement arm 942, the latter including clamping head 944. As in airway-tube holder 100, the engagement arm and thumb screw of airway-tube holder 900 couple to one another in such a way that the thumb screw has two degrees-of-freedom of motion (rotational and linear) while the engagement arm has only one degree-of-freedom of motion (linear). Clamping head 944 and tube-receiving surface 914 collectively define a clamp or adjustable aperture 958 that can immobilize an airway tube situated therein.

Thumb screw 930 includes head 936, threads 932 (which have an asymmetric profile like threads 432), and coupler 940. The coupler, which is co-axial with threads 932, extends from the forward surface of thumb screw 930.

Engagement arm 942 includes stem 950 and clamping head 944 disposed at one end thereof. Unlike the stem of engagement arm 142, the upper surface and lower surfaces of stem 950 are flat. Also unlike engagement arm 142, engagement arm 942 has coupling ring 957 disposed at end 956 of stem 950. The coupling ring receives threads 932 of thumb screw 930. This enables engagement arm 942 and thumb screw 930 to couple to one another. Furthermore, as in airway-tube holder 100, coupler 940 is received by hole 946 in clamping head 944, to secure the engagement arm and thumb screw to one another. Surface 947 of clamping head 944 is curved to facilitate engagement with the sidewall of an airway tube.

Figure 10A:
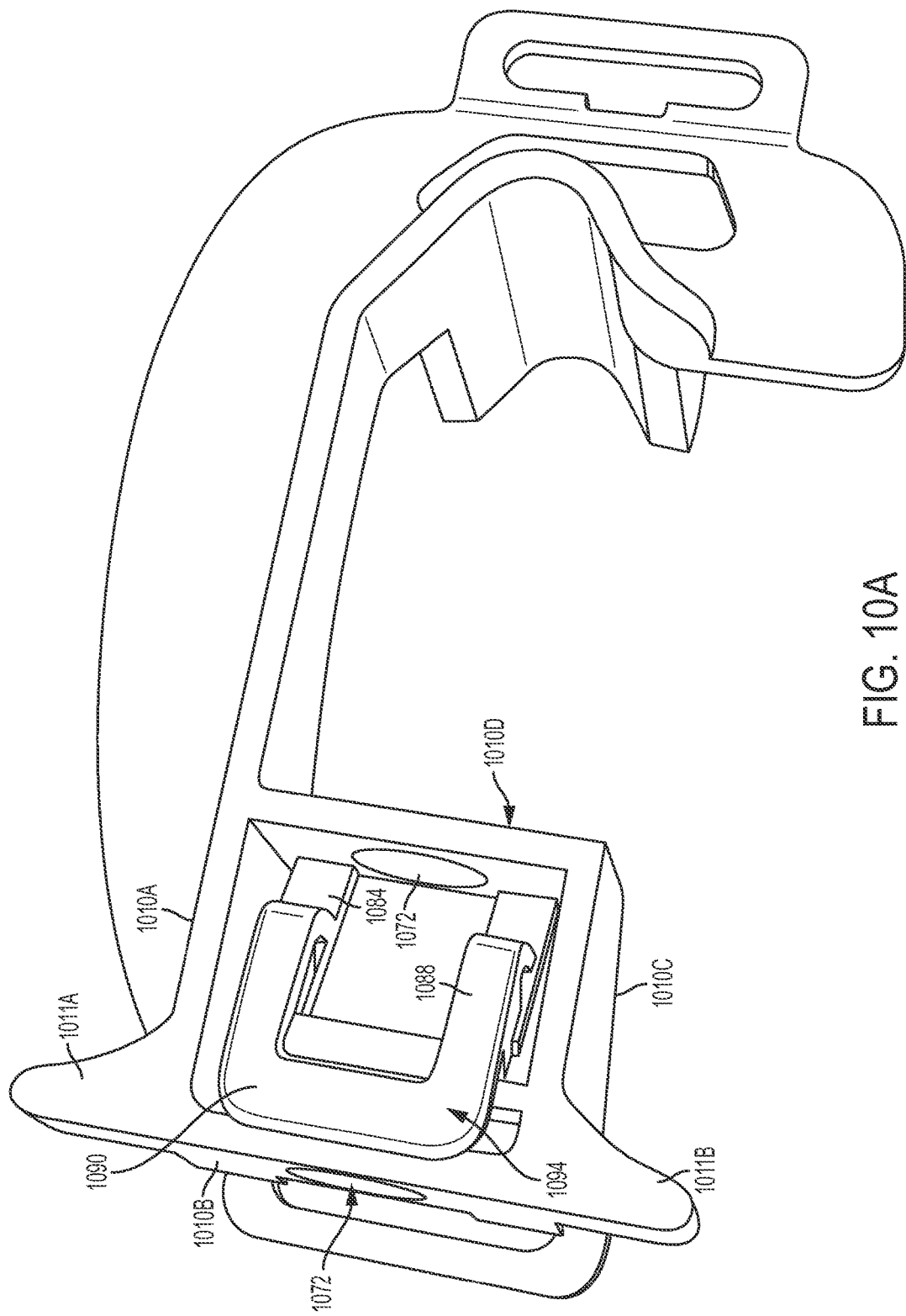
FIG. 10A depicts a top perspective view of the holding block of the airway-tube holder of FIG. 9A.
Figure 10B:
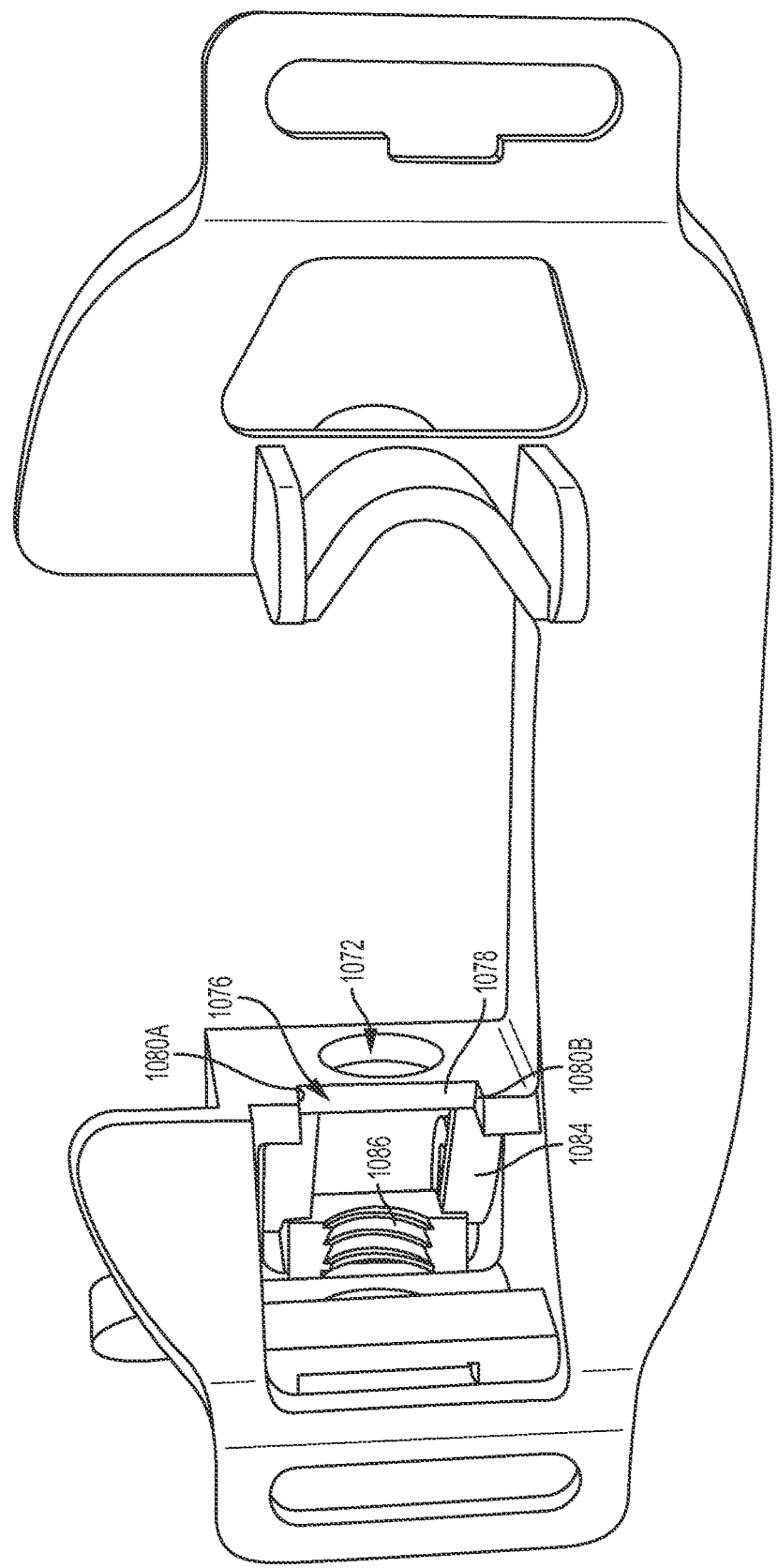
FIG. 10B depicts a bottom perspective view of the holding block of the airway-tube holder of FIG. 9A.

FIGS. 10A and 10B depict further detail of holding block 912 and the manner in which thumb screw 930 and engagement arm 942 cooperate therewith.

Referring now to FIG. 10A, holding block 912 has an approximately square perimeter, as defined by walls 1010A, 10108, 1010C, and 1010D (collectively "walls 1010"). These walls are specific segments of wall/flange 910.

Near wall 10108, wall 1010A curves "upward." Near wall 1010A, wall 10108 is extended straight "upward." The extended portions of these two walls meet to create flared region 1011A. Flared region 10118 results from the same extended configuration, although in a "downward" direction, of walls 1010C and 10108. The two flared regions 1011A and 10118 collectively define a "syringe" grip for improved ergonomics when pushing thumb screw 930 toward tube-receiving region 914.

Walls 10108 and 1010D each include openings 1072. In the illustrative embodiment, these openings are circular and receive thumb screw 930. Groove 1076 is disposed in walls 10108 and 1010D "inward" of opening 1072 therein. Each groove 1076 is defined by surface 1078 and sidewalls 1080A and 1080B. Grooves 1076 are dimensioned and arranged to receive stem 950 of engagement arm 942. As a consequence, the separation between opposing sidewalls 1080A and 1080B of each groove is slightly greater than the width of stem 950.

Two spaced-apart arms 1084 depend from wall 1010D proximal to the base thereof (i.e., relatively closer to the surface of face plate 902). Arms 1084 are angled outwardly and are capable of flexing, predominantly at the intersection with wall 1010D. As best seen in FIG. 9A, arm 1088 extends outwardly from each arm 1084. Referring again to FIG. 10B, partial female threads 1086 span the gap between the two arms 1088. The partial female threads face "inward," since these threads are located outward of thumb screw 930.

Arms 1088 continue outward, rising above walls 1010. Plate member 1090 bridges arms 1088. Plate member 1090 flares outward, continuing beyond walls 1010 in the direction of wall 10108.

Referring now to FIGS. 9A, 9B, 10A, and 10B, to assemble airway-tube holder 900, engagement arm 942 is positioned in grooves 1076 located at the "bottom" of walls 10108 and 1010D, with clamping head 944 nearest to tube-receiving surface 914. Thumb screw 930 is inserted through ring 957 in engagement arm 942, inserted through opening 1072 in wall 10108, and though opening 1072 in wall 1010D. Opening 946 in clamping head 944 of the engagement arm receives coupler 940 of thumb screw 930 to fixedly couple engagement arm 942 to the thumb screw.

The asymmetric thread profile of threads 932 enable thumb screw 930 to be pushed toward tube-receiving surface 914 with little resistance from partial female threads 1086, akin to the operation of thumb screw 130 of airway-tube holder 100. And, as in the illustrative embodiment, once clamping surface 944 is in abutting or near abutting relation with the sidewall of an airway tube, a user can turn (rather than push) thumb screw 930 to fine tune the clamping force applied to the airway tube.

Like airway-tube holder 100, the pressure applied against an airway tube by engagement arm 942/thumb screw 930 can be released in either of two ways. Either by "unscrewing" it, or by actuating quick-release mechanism 1094.

Referring again to FIGS. 9A, 9B, and 9C, arms 1084, arms 1088, and plate member 1090 collectively function as quick-release mechanism 1094 for decoupling threads 932 of thumb screw 930 from partial female threads 1086. The quick-release mechanism is actuated by lifting plate member 1090. This is in contrast to the illustrative embodiment, wherein plate member 690 is pushed to actuate the quick release function.

Lifting plate member 1090 causes partial female threads 1086 to move outwardly. This disengages partial female threads 1086 from threads 932 of thumb screw 930. Once the female threads are disengaged, thumb screw 930 can be slid away from the formerly immobilized airway tube.

Like airway-tube holder 100, the female thread does not fully surround the male threads 932 of the thumb screw. As for airway-tube holder 100, the arc length of female threads 1086 must be less than 180 degrees, and preferably less than 90 degrees to ensure that the female threads fully disengage from the male threads.

Further Alternative Embodiments

Although features such as canted strap-holding slots 116, embossed ikons 120, 692, and ribs 548 were disclosed in conjunction with airway-tube holder 100, it is to be understood that such features can be used in conjunction with airway-tube holder 900. Likewise, the syringe grip disclosed in conjunction with airway-tube holder 900 can be used in conjunction with airway-tube holder 100.

In some further alternative embodiments of an airway-tube holder, rather than including a separate engagement arm 142/942, the clamping head (i.e., clamping head 144/944) from the engagement arm can simply be coupled to the end of thumb screw 130/930. In such embodiment, the clamping head must be free to rotate independently of the thumb screw. This ensures that regardless of the rotational position of the thumb screw, the clamping head can be rotated as necessary so that its curved clamping surface has the proper orientation with respect to an airway tube. Although such embodiments are mechanically marginally simpler than the illustrative or first alternative embodiment, they are less operationally elegant and may require that the aforementioned adjustment be made by a caregiver.

In yet some further embodiments similar to those mentioned directly above, the clamping head can be weighted so that regardless of the rotational orientation of thumb 130/930, the clamping head always assumes the correct attitude with respect to the airway tube. For example, with reference to FIG. 1A, the "bottom" of clamping head 144 (the portion closest to lower partial perimeter 106 of face plate 102) would be weighted, such as with an internally placed piece of dense metal or other dense material.

It is to be understood that the disclosure describes a few embodiments and that many variations of the invention can easily be devised by those skilled in the art after reading this disclosure and that the scope of the present invention is to be determined by the following claims.

What is claimed:

1. An airway-tube holder for immobilizing an airway tube, the airway-tube holder comprising:
   a screw; and
   a face plate configured to fit over a patient's oral cavity, the face plate having a holding block that receives the screw, wherein holding block comprises at least one partial female thread, wherein the holding block and the partial female thread are physically configured so that:
   (a) the partial female thread engages threads of the screw;
   (b) the screw slides past the partial female thread when the screw is subjected to a force having a first direction and being coaxial with a long axis of the screw; and
   (c) the screw is immobilized by the partial female thread when subjected to a force having a direction opposite to the first direction.

2. The airway-tube holder of claim 1 wherein the screw has threads, and threads have an asymmetric thread profile.

3. The airway-tube holder of claim 1 wherein the holding block further comprises a first member that supports the partial female thread, wherein the first member has a configuration and location that results in generation of a counterforce that increases thread grip between the partial female threads and the threads of the screw in response to a force that results from incremental tightening of the screw.

4. The airway-tube holder of claim 3 wherein the location at which the first member is supported results in a vertical offset between an elastic-hinge point and a thread-engagement point.

5. The airway-tube holder of claim 4 and further wherein the location at which the first member is supported results in a horizontal offset between an elastic-hinge point and a thread-engagement point.

6. The airway-tube holder of claim 3 further comprising a plate member, wherein the plate member is coupled to the first member, the plate member and the first member collectively comprising a quick-release mechanism that is physically configured so that when actuated by applying, to the plate member, a force having a first direction, the partial female thread disengages from the threads of the screw.

7. The airway-tube holder of claim 6 wherein the first direction is towards the face plate, such that the force is applied by pushing the plate member.

8. The airway-tube holder of claim 6 wherein the first direction is away from the face plate, such that the force is applied by lifting the plate member.

9. The airway-tube holder of claim 6 further comprising a physical stop, wherein the stop limits movement of the plate member and the first member.

10. The airway-tube holder of claim 1 further comprising a clamping head, wherein the clamping head is coupled to the screw at a first end thereof, wherein the clamping head has an arcuate surface to facilitate coupling to the airway tube.

11. The airway-tube holder of claim 10 further comprising at least two arcuate ribs disposed on the arcuate surface of the clamping head to facilitate coupling to the airway tube.

12. The airway-tube holder of claim 1 further comprising an engagement arm, wherein the engagement arm comprises a stem and a clamping head, wherein a first end of the stem couples to the screw at a first end thereof proximal to a screw head, and the clamping head couples to the screw proximal to a second end thereof.

13. The airway-tube holder of claim 12 wherein the screw head further comprises a groove that receives the first end of the stem.

14. The airway-tube holder of claim 12 wherein the engagement arm is disposed outward of the screw relative to the face plate.

15. The airway-tube holder of claim 1 further comprising a wall extending orthogonal to a major surface of the face plate, wherein the wall forms a portion of the holding block and at least a portion of a tube receiving surface.

16. The airway-tube holder of claim 1 further comprising a left strap-retaining slot and a right strap-retaining slot, the strap-retaining slots receive a strap that couples the face plate to a patient, wherein:
  the left strap-retaining slot is disposed proximal to a left edge of the face plate and the right strap-retaining slot is disposed proximal to a right edge of the face plate, and wherein
  the strap-retaining slots are canted with respect to a vertical orientation when the face plate is in use, an upper portion of the left strap-retaining slot extending further leftward relative to a lower portion thereof and an upper portion of the right strap-retaining slot extending further rightward relative to a lower portion thereof.

17. An airway-tube holder for immobilizing an airway tube, the airway-tube holder comprising a face plate configured to fit over a patient's oral cavity, the face plate having:
  a holding block, the holding block including:
  (a) a first wall having (i) a first circular opening and (ii) a first groove therein;
  (b) a second wall spaced apart from and parallel to the first wall, the second wall having (i) a second circular opening and (ii) a second groove therein;
  (c) a first arm and a second arm, wherein the arms: (i) are spaced apart from and parallel to one another, (ii) are disposed between the first and second walls, and (iii) extend from the first wall proximal to a bottom side portion of the first wall; and
  (d) at least one partial female thread disposed between and coupled to each of the first and second arm.

18. The airway-tube holder of claim 17 wherein the partial female thread is asymmetric.

19. The airway-tube holder of claim 17 wherein the face plate further comprises a tube-receiving surface, wherein the tube-receiving surface is spaced apart from the holding block and aligns with the first circular opening and the second circular opening.

20. The airway-tube holder of claim 17 further comprising a screw, wherein threads of the screw extend through the first circular opening and the second circular opening, and further wherein the partial female thread engages the threads of the screw.

21. The airway-tube holder of claim 20 wherein the threads of the screw are asymmetric.

22. The airway-tube holder of claim 21 further comprising a plate member, wherein the plate member is coupled to the first and second arms, the plate member and the first and second arms collectively comprising a quick-release mechanism that is physically configured so that when actuated by applying a force to the plate member, the partial female thread disengage from the threads of the screw.

23. The airway-tube holder of claim 22 wherein a portion of the plate member superposes the second wall and wherein the portion of the plate member and a top of the second wall is separated by a gap having a first distance.

24. The airway-tube holder of claim 23 wherein motion of the plate member, the first and second arms, and the partial female thread is limited to the first distance.

25. The airway-tube holder of claim 20 further comprising an engagement arm, wherein the engagement arm is received by the first groove and the second groove, couples to the screw and moves in concert therewith.

26. The airway-tube holder of claim 25 wherein the face plate further comprises a tube-receiving surface, wherein the tube-receiving surface is spaced apart from the holding block and aligns with the screw and the engagement arm.

27. The airway-tube holder of claim 25 wherein the engagement arm comprises a stem and a clamping head, wherein the clamping head couples to an end of the screw, and wherein the clamping head and tube-receiving surface collectively form an adjustable aperture.

28. An airway-tube holder for immobilizing an airway tube, wherein the airway tube holder comprises a face plate configured to fit over a patient's oral cavity, the face plate having a holding block that receives a screw and an engagement arm, wherein the screw has asymmetrical threads, the engagement arm comprises a clamping head, and the engagement arm and the screw are coupled to one another, wherein the holding block comprises at least one partial female thread that is physically configured to engage the asymmetrical threads of the screw, the face plate further having a tube-receiving surface that is spaced apart from the holding block and aligns with the clamping head, wherein the screw advances the clamping head towards the tube-receiving surface when the screw is pushed, wherein the clamping head is incrementally tightenable by turning the screw, and wherein the clamping force is releasable via a quick-release mechanism that, when actuated, disengages the partial female thread from the threads of the screw.

* * * * *